(12) United States Patent
Cekic et al.

(10) Patent No.: US 6,614,028 B1
(45) Date of Patent: Sep. 2, 2003

(54) APPARATUS FOR AND METHOD OF TREATING A FLUID

(75) Inventors: Miodrag Cekic, Bethesda, MD (US); Boris Geller, Germantown, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 0 days.

(21) Appl. No.: 10/206,976

(22) Filed: Jul. 30, 2002

(51) Int. Cl.[7] .......................... G01N 21/01; G01N 21/05
(52) U.S. Cl. .............. 250/435; 250/454.11; 250/504 R; 250/432 R
(58) Field of Search ................. 250/454.11, 504 R, 250/432 R, 435

(56) References Cited

U.S. PATENT DOCUMENTS

| | | |
|---|---|---|
| 1,145,140 A | 7/1915 | Henri et al. |
| 1,307,500 A | 6/1919 | Keyes |
| 2,065,054 A | 12/1936 | Creighton et al. |
| 3,801,773 A | 4/1974 | Matsumi |
| 4,008,045 A | 2/1977 | Free |
| 4,831,268 A | 5/1989 | Fisch et al. |
| 5,034,235 A | 7/1991 | Dunn et al. |
| 5,124,131 A | 6/1992 | Wekhof |
| 5,247,178 A | 9/1993 | Ury et al. |
| 5,635,133 A | 6/1997 | Glazman |
| 5,660,719 A | 8/1997 | Kurtz et al. |
| 5,726,415 A * | 3/1998 | Luo et al. ............. 219/121.48 |
| 5,973,331 A | 10/1999 | Stevens et al. |
| 6,013,917 A | 1/2000 | Ishiyama |
| 6,013,918 A | 1/2000 | Bushnell et al. |
| 6,083,387 A * | 7/2000 | LeBlanc et al. ............ 210/199 |
| 6,433,344 B1 * | 8/2002 | Salisbury et al. ........ 250/455.11 |

FOREIGN PATENT DOCUMENTS

| | | |
|---|---|---|
| FR | 2 555 567 | 5/1985 |
| WO | 90/06899 | 6/1990 |
| WO | 96/33135 | 10/1996 |

* cited by examiner

Primary Examiner—John R. Lee
Assistant Examiner—James J Leybourne
(74) Attorney, Agent, or Firm—Antonelli, Terry, Stout & Kraus, LLP

(57) ABSTRACT

An apparatus for and a method of treating a volume of fluid. The apparatus includes a fluid passageway through which the fluid flows, at least one source of irradiation, external to the fluid passageway, and at least two elongated elliptical reflecting troughs for reflecting irradiation from the at least one source of irradiation onto the fluid passageway. Open ends of the troughs face each other to define a space between the closed ends of the troughs. The fluid passageway and the at least one source of irradiation are positioned in the space, with each source of irradiation within a respective one of the at least two troughs. At least one of the fluid passageway and the at least one source of irradiation is spaced from the focal axes so as to provide a substantially uniform irradiation distribution within the fluid in the fluid passageway.

75 Claims, 11 Drawing Sheets

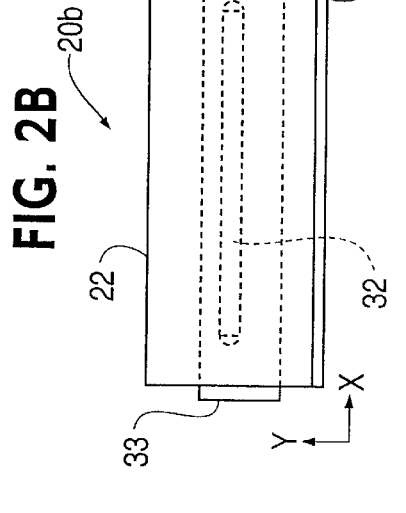
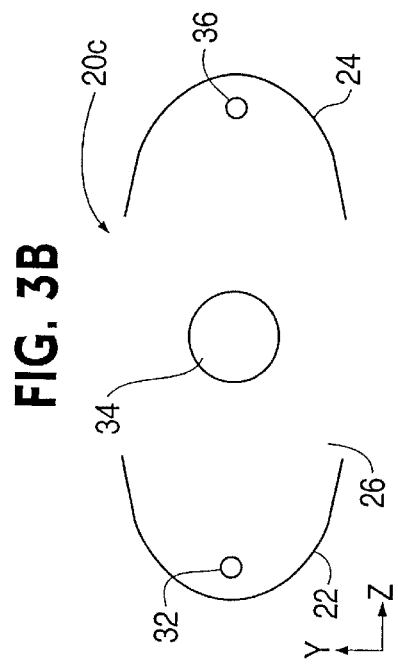
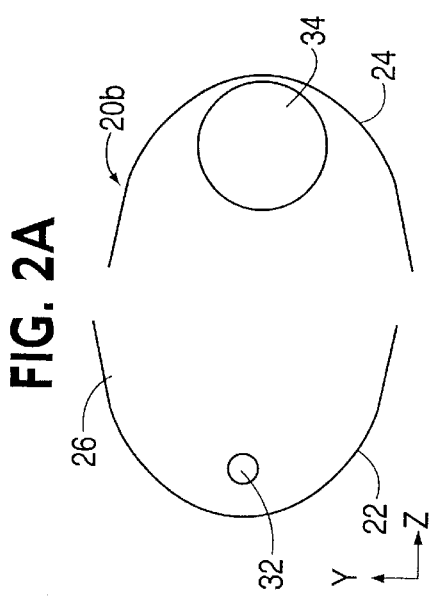
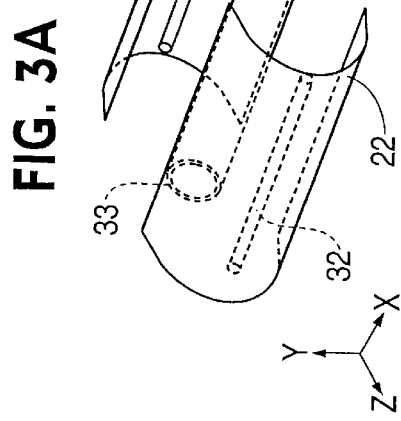

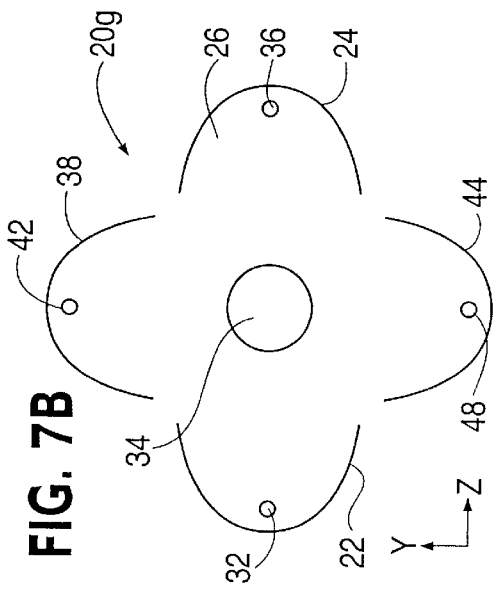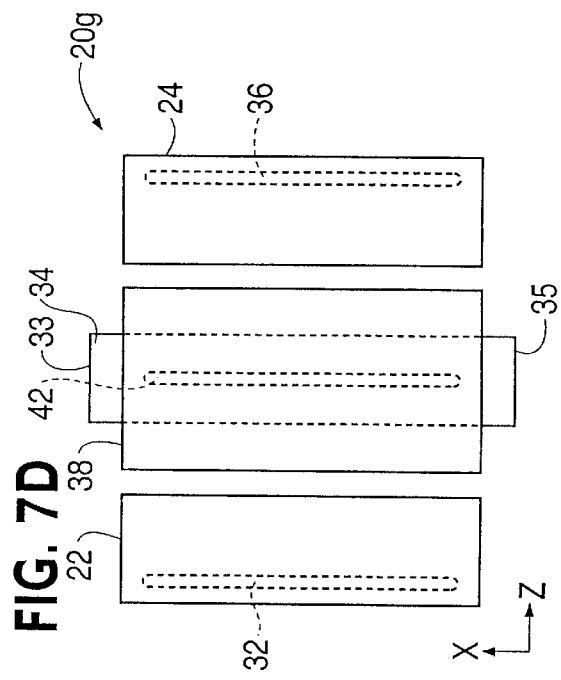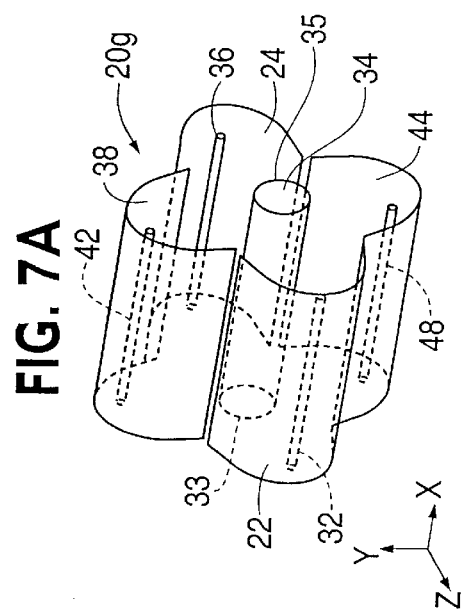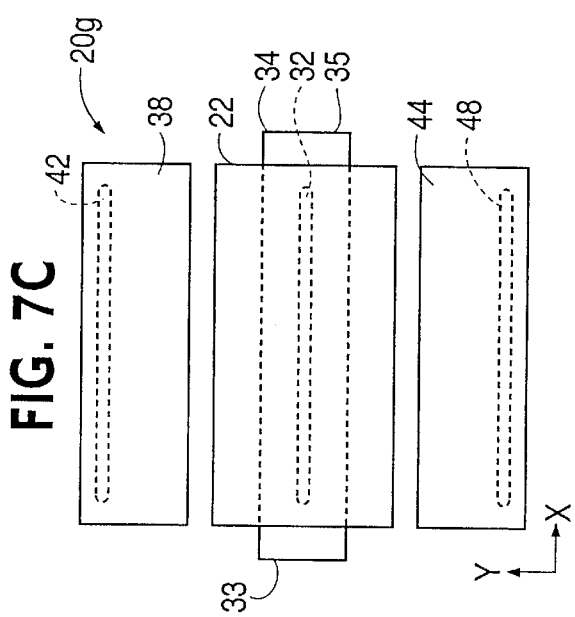

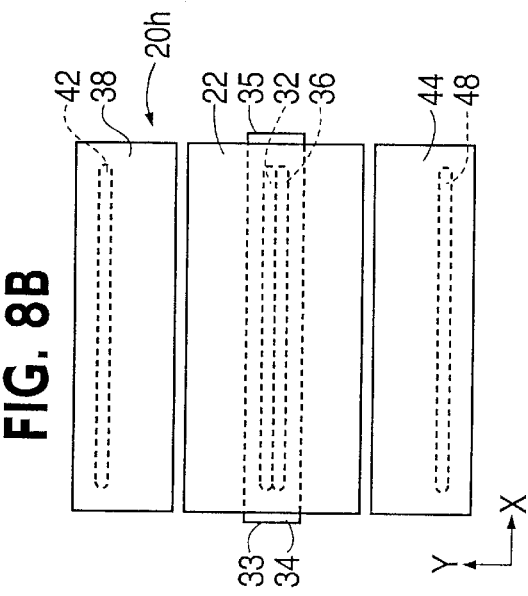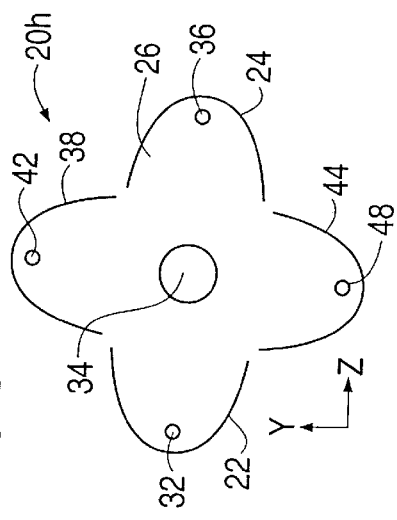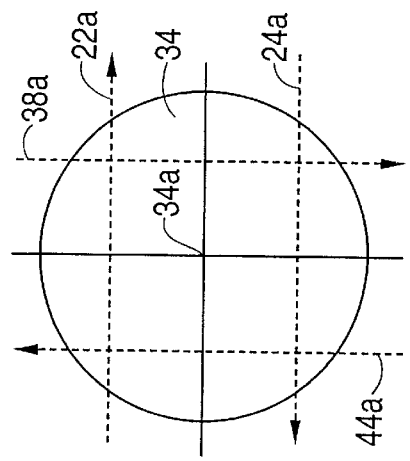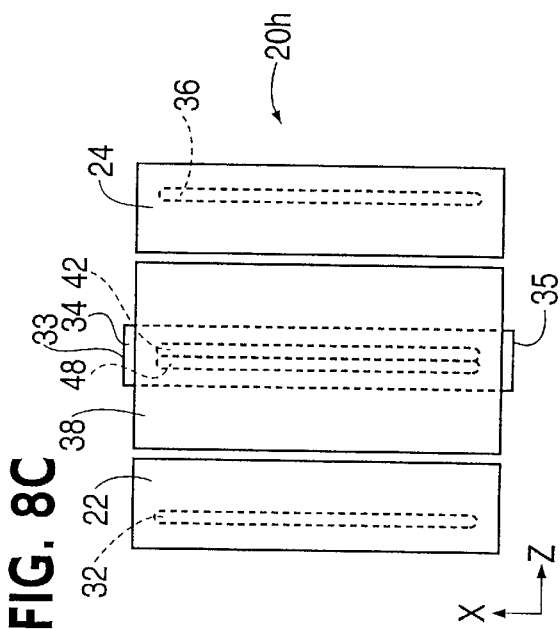

APPARATUS FOR AND METHOD OF TREATING A FLUID

FIELD OF THE INVENTION

The present invention pertains to an apparatus for and a method of uniform treatment of fluid volumes using external irradiation sources. More particularly, the present invention pertains to an apparatus for and a method of treating a volume of fluid in a fluid passageway by irradiating the fluid passageway from an external irradiation source to provide a substantially uniform irradiation distribution within the fluid in the fluid passageway.

BACKGROUND OF THE INVENTION

During the irradiation treatment of fluids flowing through fluid passageways, the uniformity of irradiation is of primary importance. By way of example, the fluid might be treated with ultraviolet irradiation so as to disinfect, purify, or cause oxidation of material within the fluid. If the irradiation is not uniform, those portions of the fluid flowing through the regions of low irradiation intensity may be undertreated, while portions in the vicinity of peak irradiation fields may receive higher than desired doses of irradiation which could damage material within the fluid. This problem is even more significant in the case of turbid fluids or fluids of high absorptivity for the applied irradiation.

Known techniques for irradiation of volumes of fluid include immersing multiple irradiation sources in the fluid. However, this is complex and costly, requiring multiple irradiation sources and introducing additional problems of cumulative absorption caused by impurities on the irradiation source-fluid interface. Cleaning mechanisms and processes have been proposed to overcome this last problem, but these are likewise elaborate and complex. Potential irradiation source accidents introduce additional risks of pollution of the fluid and the distribution system by the hazardous irradiation source components.

A second approach is to restrict the fluid flow, avoiding underexposed volumes. This scheme suffers from limited efficiency, high pressure drops, and high cost of pumps necessary to achieve the desired flow.

Another approach is to introduce mixing devices in the fluid flow, in the hope that each portion of the fluid will receive an "average" treatment. This approach likewise suffers from efficiency problems, as well as the more serious problems of likely undertreatment of a portion of the fluid volume.

A further approach is to present the fluid as a thin film to the irradiation. This approach does not take into account the absorption of the source, the fluid passageway, and the fluid itself, nor the indices of refraction of the fluid passageway material or the fluid, and hence the real energy distribution in the thin film of fluid.

SUMMARY OF THE INVENTION

The present invention is an apparatus for and a method of uniformly treating fluid volumes. In accordance with the present invention a fluid passageway is provided, through which the fluid flows. At least one source of irradiation, external to the fluid passageway, produces irradiation to irradiate the fluid flowing within the fluid passageway. The apparatus further includes at least two elongated elliptical reflecting troughs for reflecting light from the at least one source of irradiation onto the fluid flowing within the fluid passageway. The troughs have openings facing each other to define a space between the closed elliptical ends of the troughs. The ellipse of each trough has a first focal point within the trough, the locus of which over the length of the troughs defines a first focal axis. Further, the ellipse of each trough has a second focal point outside the trough, the locus of which defines a second focal axis. The fluid passageway and each source of irradiation are positioned in the space. At least one of the fluid passageway and the at least one source of irradiation is spaced from the focal axes of the troughs so that the irradiation irradiating the fluid passageway is defocused. As a consequence, the fluid in the passageway is irradiated with a substantially uniform irradiation distribution, even in a fluid passageway of relatively large internal diameter.

BRIEF DESCRIPTION OF THE DRAWINGS

These and other aspects and advantages of the present invention are more apparent from the following detailed description and claims, particularly when considered in conjunction with the accompanying drawings. In the drawings:

FIGS. 2A and 2B are, respectively, a cross-sectional view and a side view of a second embodiment of an apparatus in accordance with the present invention, the perspective view and top view being similar to FIGS. 1A and 1D, respectively;

FIGS. 3A, 3B and 3C are, respectively, a perspective view, a cross-sectional view, and a top view of a third embodiment of an apparatus in accordance with the present invention, the side view being similar to FIG. 1C;

FIGS. 7A, 7B, 7C and 7D are, respectively, a perspective view, a cross-sectional view, a side view and a top view of a seventh embodiment of an apparatus in accordance with the present invention;

FIGS. 8A, 8B, and 8C are, respectively, a cross-sectional view, a side view and a top view of an eighth embodiment of an apparatus in accordance with the present invention, the perspective view being similar to FIG. 7A;

FIG. 8D is an enlarged cross-sectional view of the fluid passageway of the apparatus of FIGS. 8A–8C;

DETAILED DESCRIPTION OF PREFERRED EMBODIMENTS

Figure 1A:
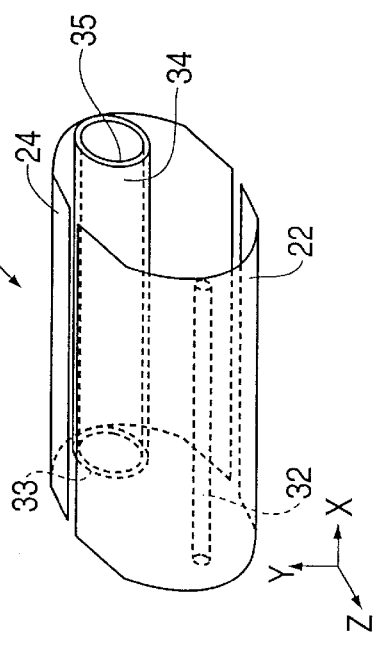
FIG. 1A is a perspective view illustrating a first embodiment of an apparatus and a method in accordance with the present invention.
Figure 1B:
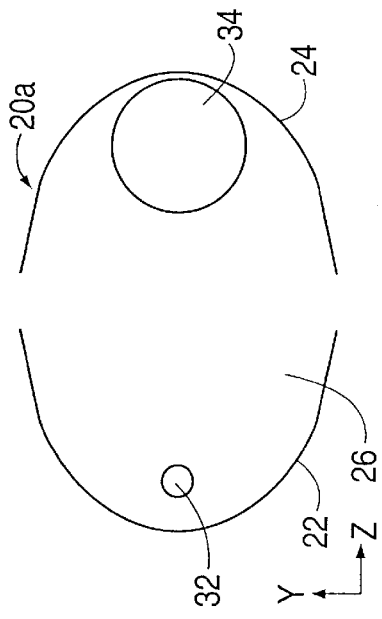
FIG. 1B is a cross-sectional view of the apparatus of FIG. 1A.
Figure 1C:
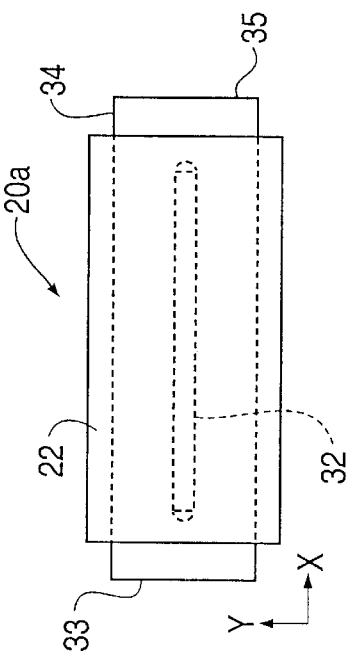
FIG. 1C is a side view of the apparatus of FIG. 1A.
Figure 1D:
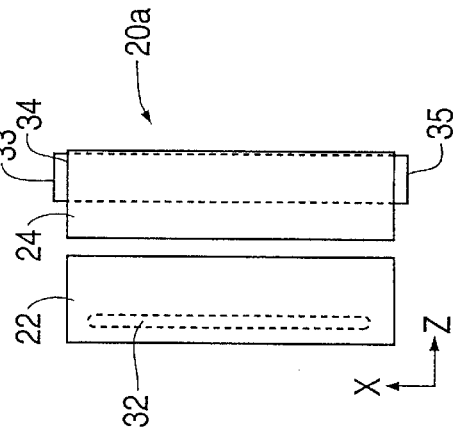
FIG. 1D is a top view of the apparatus of FIG. 1A.

FIGS. 1A–1D depict a first embodiment of an apparatus 20a in accordance with the present invention. Apparatus 20a includes a first elongated elliptical reflecting trough 22 and a second elongated elliptical reflecting trough 24. Each trough 22, 24 has a closed elliptical end and an open end. Troughs 22 and 24 define an ellipse having a major axis and a minor axis and having a first focal axis within trough 22 and a second focal axis within trough 24. If desired, the open ends of troughs 22 and 24 may be connected by reflective members. Troughs 22 and 24 cooperate to define a space 26 within apparatus 20a.

A source of irradiation 32 is positioned within trough 22, and so within space 26. Irradiation source 32 is on the major axis of the ellipse defined by troughs 22 and 24, at or adjacent the focal axis within trough 22. Irradiation source 32 might be a light source such as a source of ultraviolet light. By way of example, irradiation source 32 might be a microwave electrodeless discharge bulb, such as a tubular bulb, or might be an arc discharge bulb or a fluorescent discharge bulb. Also within space 26 a fluid passageway 34 is positioned at or adjacent the focal axis within trough 24. Fluid passageway 34 has an inlet end 33, which is adapted to be connected to a source of fluid to be treated, and an outlet end 35, which is adapted to be connected to a destination for the fluid after treatment. In the embodiment of FIGS. 1A–1D, either irradiation source 32 or fluid passageway 34, or both, is spaced from the adjacent focal axis. If desired, an adjustable mount can be provided making the position of irradiation source 32 adjustable. The mount might be adjustable on trough 22 or another mounting surface, or irradiation source 32 might be adjustable on the mount. Additionally, or alternatively, an adjustable mount can be provided making the position of fluid passageway 34 adjustable. This mount might be adjustable on trough 24 or another mounting surface, or fluid passageway 34 might be adjustable on the mount. As a consequence, the irradiation from source 32 is not focused on fluid passageway 34. Therefore, irradiation from source 32 irradiates the fluid within fluid passageway 34 with a substantially uniform irradiation distribution. The irradiation has a substantially two-dimensionally uniform irradiation distribution across the cross-section of fluid passageway 34, as well as a substantially three-dimensionally uniform irradiation distribution within the volume of fluid in the fluid passageway.

FIGS. 2A and 2B depict a second embodiment of an apparatus 20b in accordance with the present invention. Apparatus 20b differs from apparatus 20a of FIGS. 1A–1D in that one or both of the troughs 22, 24 of apparatus 20b are shifted along axes parallel with the minor axis of the shifted trough so that the troughs 22, 24, do not have coincident major axes, and so do not define a single ellipse. The major axes of the two troughs are preferably parallel. Again, the irradiation from source 32 is defocused as it reaches fluid passageway 34, and so the irradiation has a substantially uniform distribution within the fluid in the passageway.

Figure 3C:
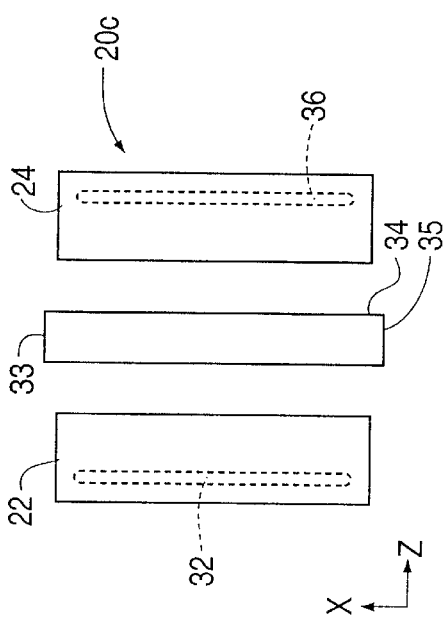

FIGS. 3A, 3B and 3C are, respectively, a fragmentary perspective view, a cross-sectional view, and a top view of a third embodiment of an apparatus 20c in accordance with the present invention. The end view of this embodiment is similar to FIG. 1C. Apparatus 20c includes first and second troughs 22 and 24, each of which is a portion of a separate ellipse. The open ends of troughs 22 and 24 face each other to define a space 26 within apparatus 20c. If desired the open ends of troughs 22 and 24 may be connected by reflective members. Each trough 22, 24 of this embodiment has a first focal axis within the trough and a second focal axis beyond the open end of the trough. The second focal axes of the two troughs coincide. A first irradiation source 32 is positioned at or adjacent the first focal axis of trough 22, and a second irradiation source is positioned at or adjacent the first focal axis of trough 24. Fluid passageway 34 is positioned at or adjacent the coincident second focal axes. Either the two irradiation sources 32 and 36 are spaced from their respective first focal axes or fluid passageway 34 is spaced from the coincident second focal axes, or both. As a consequence, the irradiation from sources 32 and 36 is not focused on fluid passageway 34, and so irradiation from the sources irradiates the fluid within passageway 34 with a substantially uniform irradiation distribution.

Figure 4A:
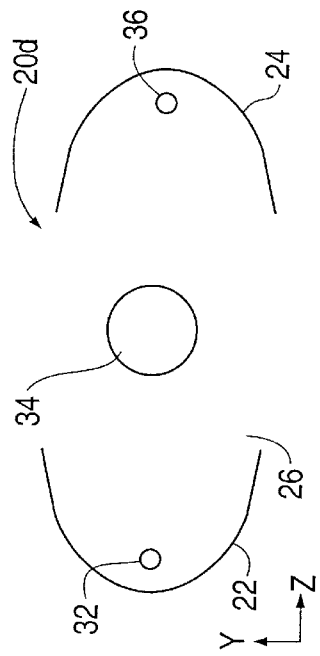
FIGS. 4A and 4B are, respectively, a cross-sectional view and a side view of a fourth embodiment of an apparatus in accordance with the present invention, the perspective and top views being similar to FIGS. 3A and 3C, respectively.
Figure 4C:
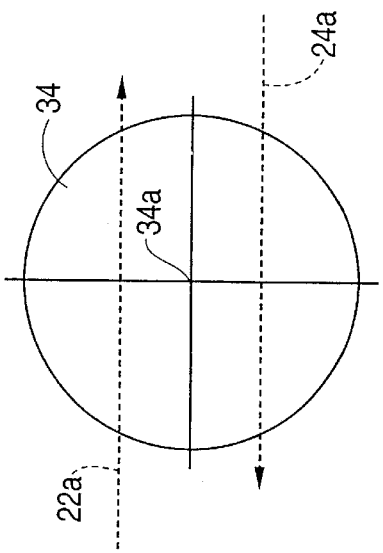
FIG. 4C is an enlarged cross-sectional view of the fluid passageway in the apparatus of FIG. 4A and 4B.
Figure 4B:
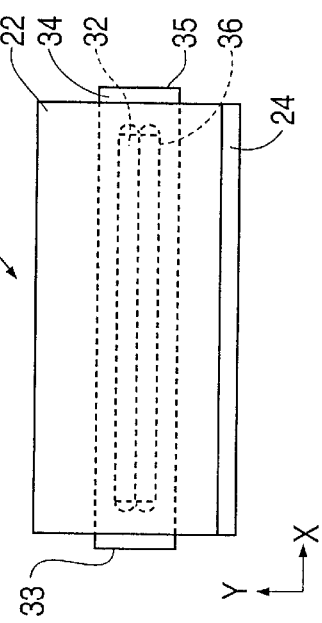
Figure 5B:
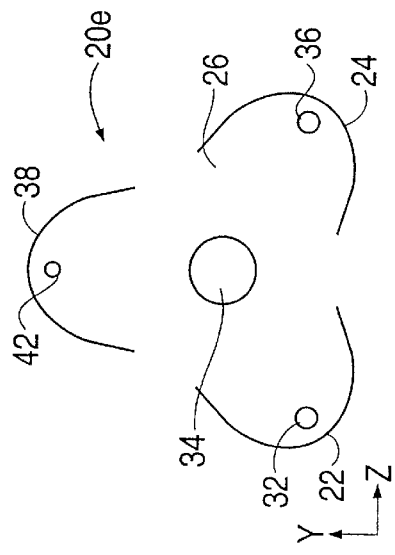
FIGS. 5A, 5B, 5C, and 5D are, respectively, a perspective view, a cross-sectional view, a side view, and a top view of a fifth embodiment of an apparatus in accordance with the present invention.
Figure 5D:
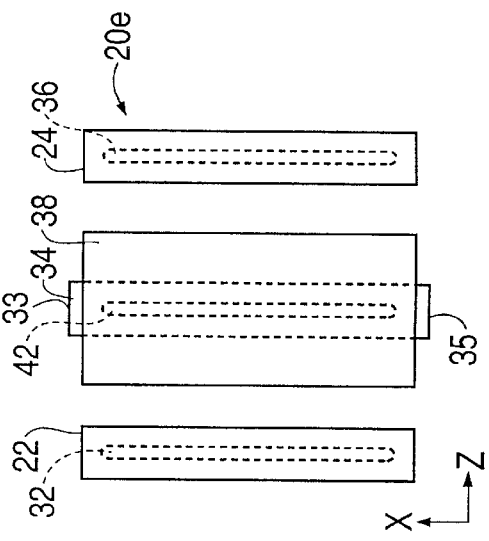
Figure 5A:
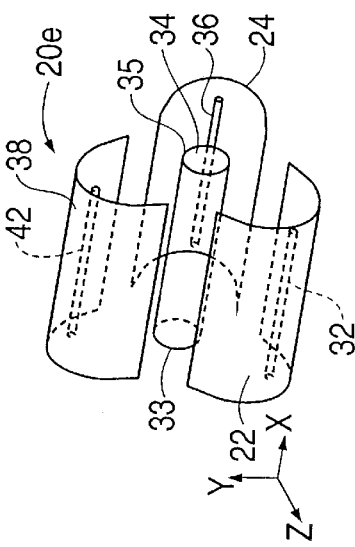
Figure 5C:
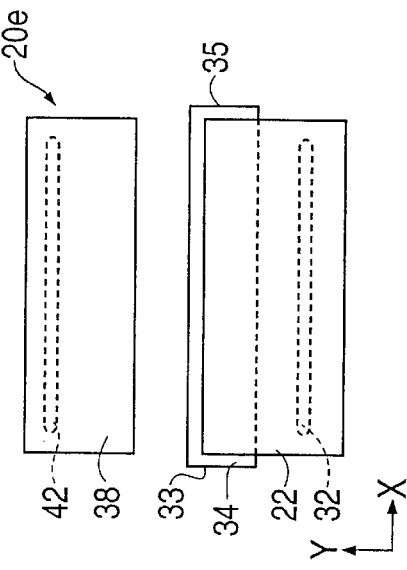

FIGS. 4A and 4B depict a fourth embodiment of an apparatus 20d in accordance with the present invention. Apparatus 20d differs from apparatus 20c of FIGS. 3A–3C in that one or both of the troughs 22, 24 of apparatus 20d are shifted along axes parallel with the minor axis of the shifted trough so that the troughs do not have coincident major axes and do not define a single ellipse. The major axes 32a, 36a are preferably parallel. Because of this shifting, the irradiation from source 32 is defocused as it reaches fluid passageway 34, and so the irradiation has a substantially uniform distribution within the fluid in the passageway.

FIG. 4C depicts the major axes 22a and 24a of elliptical reflecting troughs 22 and 24 of apparatus 20d passing through fluid passageway 34 when the two elliptical reflecting troughs 22, 24 are shifted in opposite directions parallel with their minor axes. Preferably, fluid passageway 34 has an axis 34a which extends parallel with the longitudinal axes of irradiation sources 32 and 36 and is positioned substantially midway between the major axes 22a and 24a.

FIGS. 5A, 5B, 5C, and 5D depict, respectively, a perspective view, a cross-sectional view, a side view, and a top view of another embodiment of an apparatus 20e in accordance with the present invention. Apparatus 20e includes three troughs 22, 24, and 38, and three irradiation sources 32, 36 and 42, together with fluid passageway 34. The troughs are positioned so that apparatus 20e has a somewhat triangular configuration with a space 26 within apparatus 20e. If desired, the adjacent open ends of troughs 22, 24, 38 may be joined by reflective members. Fluid passageway 34 is in substantially the center of space 26. Each irradiation source 32, 36, and 42 is at or adjacent the first focal axis of its respective elliptical reflecting trough 22, 24, 38. The second focal axes of each reflecting trough 22, 24, 38 coincide, and fluid passageway 34 is at or adjacent the coincident second focal axes. Either the irradiation sources 32, 36 and 42 are spaced from their respective first focal axes, or fluid passageway 34 is spaced from the second focal axes, or both. Such positioning results in the irradiation from sources 32, 36, and 42 being defocused on fluid passageway 34 so that the fluid in the passageway is irradiated with a substantially uniform irradiation distribution.

Figure 6A:
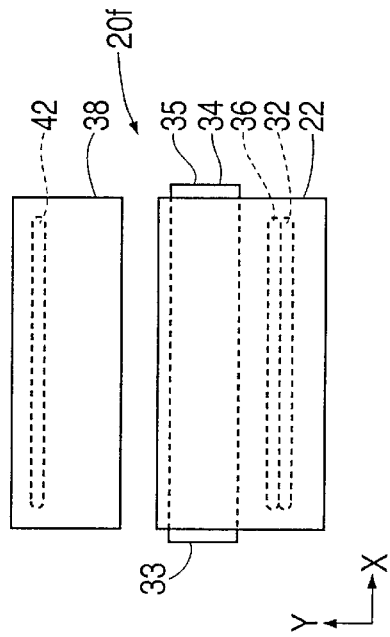
FIGS. 6A, 6B and 6C are, respectively, a cross-sectional view, a side view, and a top view of a sixth embodiment of an apparatus in accordance with the present invention, the perspective view being similar to FIG. 5A.
Figure 6B:
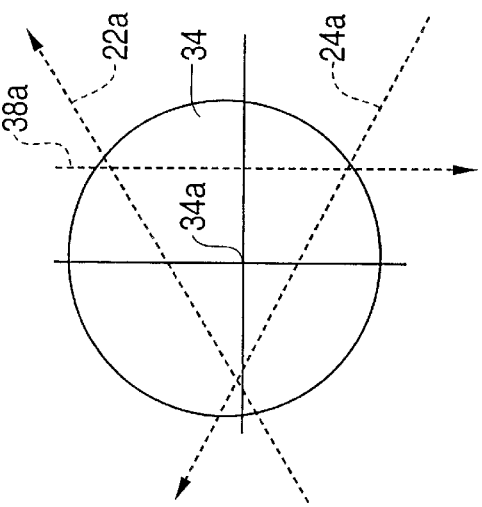
Figure 6C:
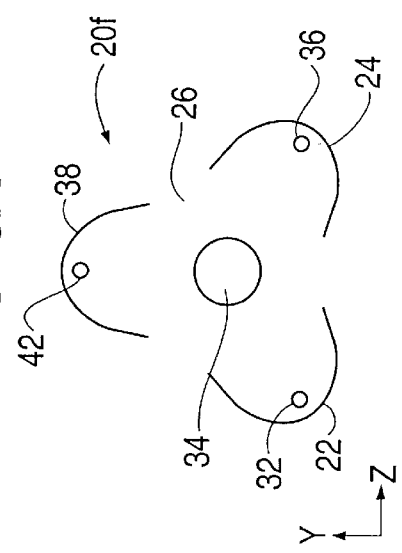

FIGS. 6A, 6B, and 6C depict a sixth embodiment of an apparatus 20f in accordance with the present invention in which the troughs are shifted in the same relative direction along the minor axes of the respective troughs from their position in apparatus 20e of the embodiment of FIGS. 5A–5D. This shifting likewise results in the irradiation on fluid passageway 34 being defocused so that the fluid within the passageway is irradiated with a substantially uniform irradiation distribution.

Figure 6D:
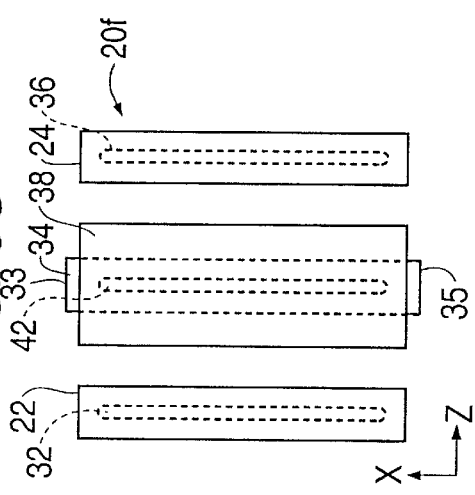
FIG. 6D is an enlarged cross-sectional view of the fluid passageway in the apparatus of FIGS. 6A–6C.

FIG. 6D depicts the major axes 22a, 24a, and 38a of elliptical reflecting troughs 22, 24, and 38 in an apparatus 20f in which each trough 22, 24, 38 has been shifted in the same relative direction along its minor axis, as the major axes pass through fluid passageway 34. The major axes define a geometric figure within the cross-section of fluid passageway 34. Fluid passageway 34 has a central axis 34a which preferably extends parallel with the longitudinal axes of irradiation sources 32, 36, and 42 and within the geometric figure defined by the major axes 22a, 24a, and 38a of apparatus, preferably at substantially the center of that figure.

FIGS. 7A, 7B, 7C and 7D depict a seventh embodiment of an apparatus 20g in accordance with the present invention. Apparatus 20g includes four troughs 22, 24, 38 and 44, and four irradiation sources 32, 36, 42, and 48, one irradiation source being at or adjacent the first focal axis of each trough. The troughs are positioned so that the major axes of troughs 22 and 24 coincide and are substantially perpendicular to the major axes of troughs 38 and 44, which likewise coincide. If desired, the adjacent open ends of troughs 22, 24, 38 and 44 may be joined by reflective members. The second focal axes of troughs 22, 24, 38, and 44 preferably coincide. Fluid passageway 34 is within space 26 in apparatus 20g, at or adjacent the second focal axes. Irradiation sources 32, 36, 42, and 48 are spaced from the respective first focal axes, or fluid passageway 34 is spaced from the second focal axes, or both. Positioning in any of these manners results in the irradiation from sources 32, 36, 42 and 48 being defocused on fluid passageway 34 so that fluid within the passageway is irradiated with a substantially uniform irradiation distribution. If desired, adjustable mounts can be provided making the positions of irradiation sources 32, 36, 42, and 48 adjustable along the major axes of their respective troughs. The mounts might be adjustable on the troughs or another mounting surface, or the irradiation sources might be adjustable on the mounts.

FIGS. 8A, 8B, and 8C depict a further embodiment of an apparatus 20h in accordance with the present invention. Apparatus 20h differs from apparatus 20g of FIGS. 7A–7D in that each of the troughs 22, 24, 38 and 44 is shifted in the same relative direction parallel to its minor axis so that the major axes 22a, 24a, 38a, and 44a define a geometric pattern on the cross-section of fluid passageway 34, as depicted in FIG. 8D. If desired, adjustable mounts can be provided making the positions of troughs 22, 24, 38, and 44 and irradiation sources 32, 36, 42 and 46 adjustable in the directions of the minor axes of the respective troughs or in the direction of the major axis of the respective troughs, or both. The mounts might be adjustable on a mounting surface, or the troughs might be adjustable on the mounts. Fluid passageway 34 has a central axis 34a which preferably extends parallel with the longitudinal axes of irradiation sources 32, 36, 42, and 46. Central axis 34a is within the geometric pattern defined by longitudinal axes 22a, 24a, 38a and 44a, preferably, at substantially the center of that geometric figure.

Figure 9:
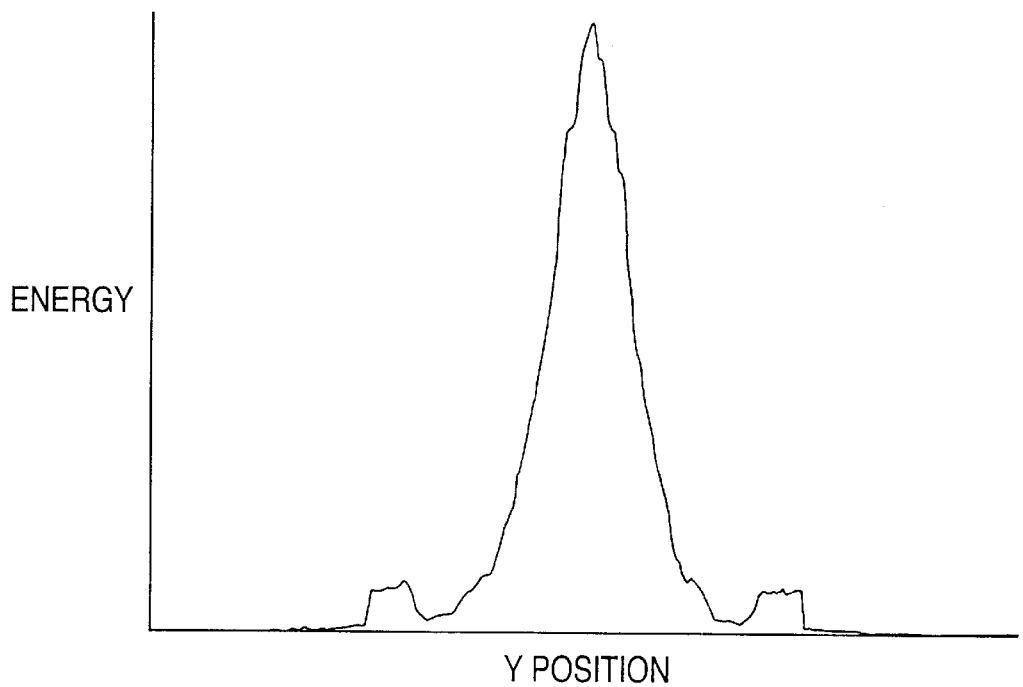
FIG. 9 illustrates an irradiance pattern of an apparatus having the irradiation source and the fluid passageway on respective focal axes of the troughs.
Figure 12:
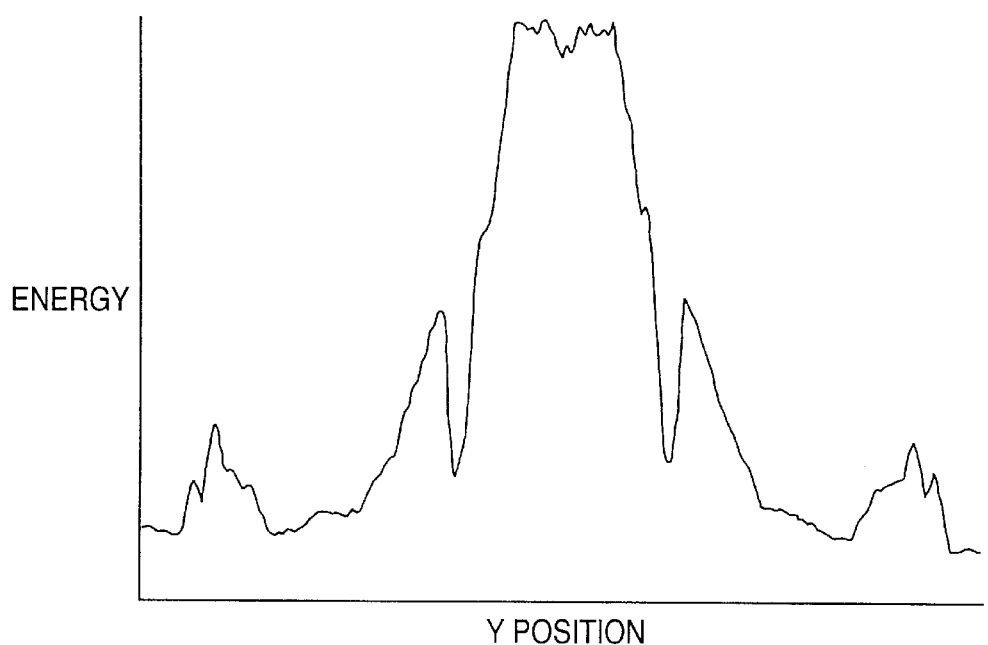
FIG. 12 illustrates the irradiance pattern of the apparatus of FIGS. 8A–8C.
Figure 13:
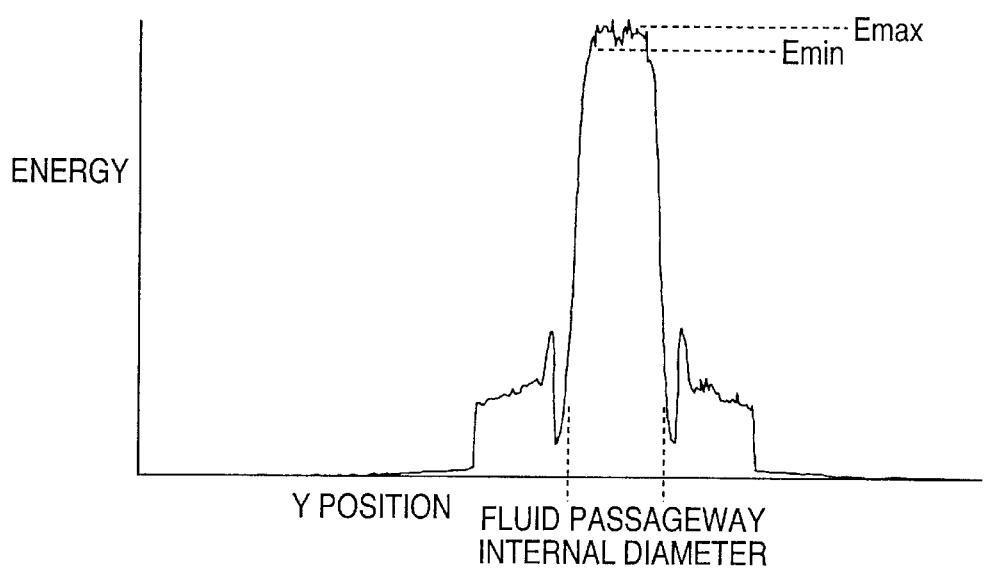
FIG. 13 is an irradiance pattern that illustrates the definition of peak intensity deviation.
Figure 14:
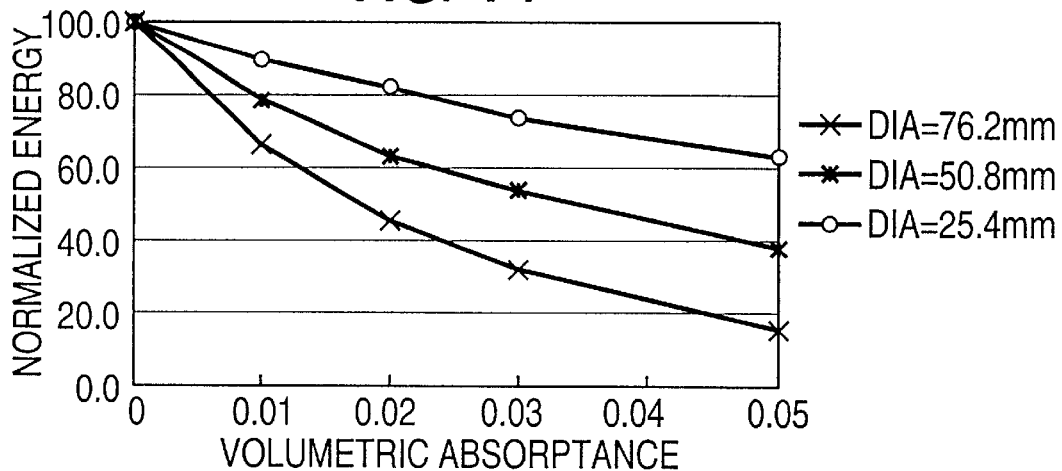
FIGS. 14, 15, and 16 illustrate normalized energy as a function of volumetric absorptance for the apparatus of FIGS. 2A and 2B, FIGS. 4A and 4B, and FIGS. 8A–8C, respectively.
Figure 15:
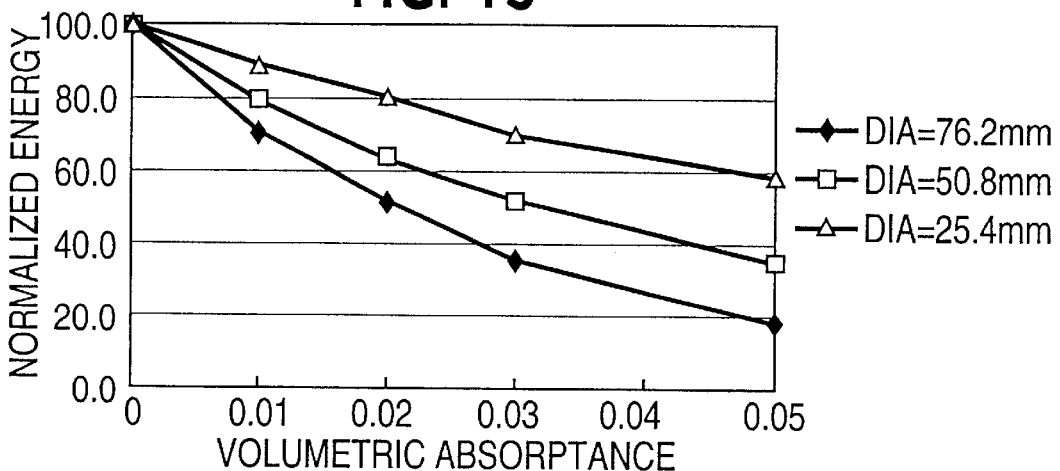
Figure 16:
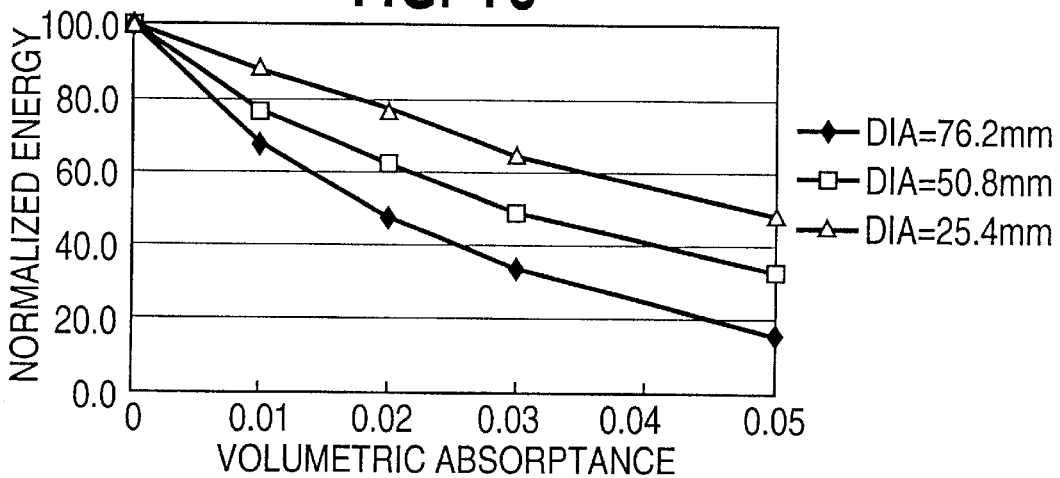

FIGS. 9–13 illustrate irradiation patterns and FIGS. 14–16 illustrate normalized energy as a function of volumetric absorptance of various apparatuses. These figures were obtained from computer simulations of the various apparatuses. FIG. 9 illustrates the Y-direction irradiation pattern of an apparatus having a single source of irradiation, similar to apparatus 20a of FIGS. 1A–1D, but with the irradiation focused by positioning irradiation source 32 on the first focal axis of the ellipse defined by troughs 22 and 24 and positioning fluid passageway 34 on the second focal axis. The X, Y, and Z axes are illustrated in FIGS. 1A–1D. As can be seen, the irradiation is sharply focused. This will not result in a uniform irradiation distribution within the fluid in fluid passageway 34.

Figure 10:
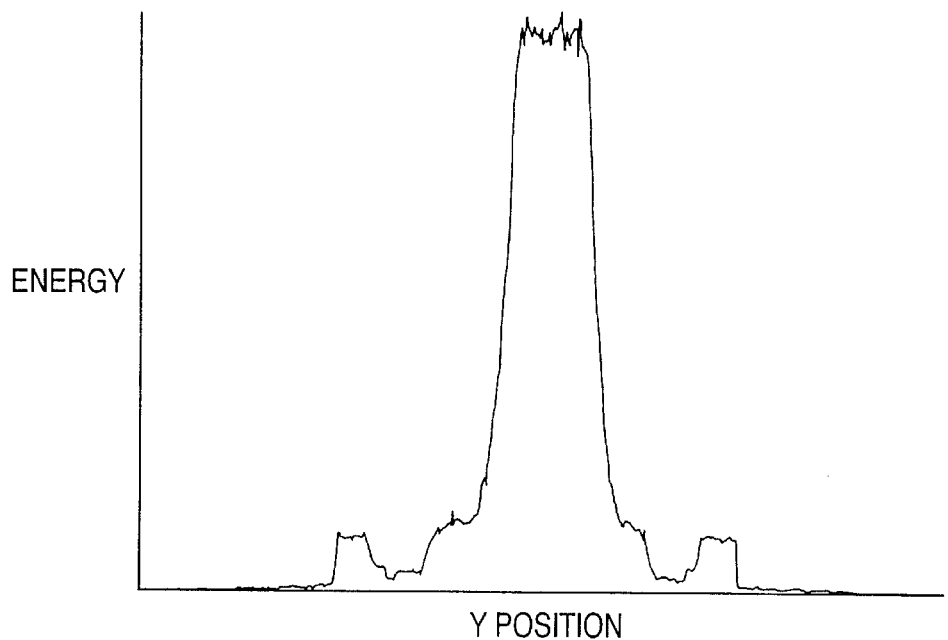
FIG. 10 illustrates the irradiance pattern of the apparatus of FIGS. 2A and 2B.

FIG. 10 illustrates the Y-direction irradiation pattern of the apparatus 20b of FIGS. 2A and 2B, the X, Y and Z axes being shown in FIGS. 2A and 2B. The defocusing of the irradiation by the shifting of one or both of the troughs in their Y directions and by spacing of irradiation source 32 from the first focal axis of trough 22 or spacing of fluid passageway 34 from the second focal axes of troughs 22 and 24, or both, results in the irradiation distribution being substantially uniform within the fluid in fluid passageway 34.

As can be seen by comparison of FIGS. 9 and 10, defocusing of the irradiation, in accordance with the present invention, substantially increases the uniformity of the irradiation distribution within the fluid in fluid passageway 34.

Figure 11:
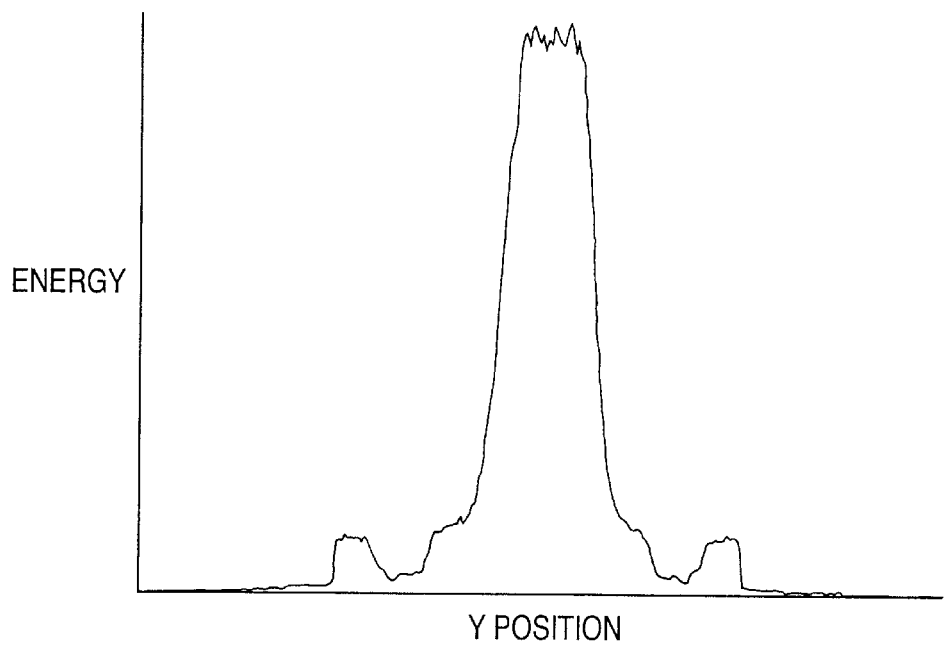
FIG. 11 illustrates the irradiance pattern of the apparatus of FIGS. 4A and 4B.

FIG. 11 illustrates the Y-direction irradiation pattern of apparatus 20d of FIGS. 4A and 4B, the X, Y and Z axes being shown in FIGS. 4A and 4B. Defocusing of the irradiation by shifting one or both of the elliptical reflecting troughs 22, 24 in their Y directions and by spacing of irradiation sources 32 and 36 from the first focal axes of troughs 22 and 24 or spacing of fluid passageway 34 from the second focal axes of the troughs, or both, results in the irradiation distribution being substantially uniform within the fluid in fluid passageway 34.

FIG. 12 illustrates the Y-direction irradiation pattern on the fluid within fluid passageway 34 in the apparatus 20h of FIGS. 8A–8C, the X, Y and Z axes being shown in FIGS. 8A–8C. Defocusing of the irradiation results in the irradiation distribution being substantially uniform within the fluid in fluid passageway 34.

FIGS. 13 depicts a irradiation distribution and illustrates the definition of peak intensity deviation. The irradiation distribution reaches a substantially uniform peak having a width substantially corresponding with the internal diameter of a fluid passageway such as fluid passageway 34. Nevertheless that peak has maximum and minimum fluctuations as depicted in FIG. 13. The peak intensity deviation $\Delta=(E_{max}-E_{min})\div(E_{max}+E_{min})\%$ as $E_{max}$ and $E_{min}$ are defined in FIG. 13.

The following table, based on computer simulations, shows the relationship between the volumetric absorptance and the peak intensity deviation in a fluid passageway having an inner diameter of three inches in the apparatus of FIGS. 4A–4C. As can be seen, even with relatively high volumetric absorptance, the peak intensity deviation is very low due to the substantially uniform irradiation distribution within the fluid in the fluid passageway.

| Volumetric absorptance, α (mm⁻¹) | Δ = (Emax − Emin) ÷ (Emax + Emin), % |
|---|---|
| 0.00 | <±0.5% |
| 0.01 | ±1.5% |
| 0.02 | ±3.5% |
| 0.03 | ±5.5% |
| 0.05 | ±9.6% |

FIG. 14 shows the normalized energy of the apparatus of FIG. 2A and 2B as a function of volumetric aborptance α for fluid passageways of various internal diameters. FIG. 15 similarly shows the normalized energy of the apparatus of FIGS. 4A and 4B as a function of volumetric absorptance a for fluid passageways of various internal diameters. FIG. 16 likewise shows the normalized energy of the apparatus of FIGS. 8A–8C as a function of volumetric absorptance a for fluid passageways of various internal diameters. In FIGS. 14–16, all curves are normalized at α=0.00. (The energy level is 100% at α=0.0). As can be seen, even with relatively high volumetric absorptance, the irradiation distribution is substantially uniform.

The present invention thus provides an improved apparatus for and method of treatment of fluids. Fluid can be treated by passing it through the fluid passageway of an apparatus in accordance with the present invention and irradiating the fluid with a substantially uniform irradiation distribution. While apparatuses with 2, 3, and 4 reflecting troughs have been illustrated, any number N of troughs could be provided, with the major axis of each trough intersecting the major axis of its angularly adjacent troughs at an angle 2π/N, where N is the number of troughs. Although the invention has been described with reference to preferred embodiments, various alterations, rearrangements, and substitutions might be made, and still the result would be within the scope of the invention.

What is claimed is:

1. Apparatus for treating a volume of fluid, said apparatus comprising:
   a fluid passageway through which the fluid flows;
   at least one source of irradiation, external to said fluid passageway; and
   at least two elongated elliptical reflecting troughs for reflecting irradiation from said source of irradiation onto said fluid passageway, each trough having a closed elliptical end and an open end, the open ends facing each other to define a space between the closed ends of said troughs, each trough having first and second focal axes, a major axis, and minor axis, wherein:
   each of said fluid passageway and said at least one source of irradiation is positioned in the space between the closed ends of said troughs, with each source of irradiation within a respective one of said at least two troughs, and
   at least one of said fluid passageway and said at least one source of irradiation is spaced from said focal axes so as to provide a substantially uniform irradiation distribution within the fluid in said fluid passageway.

2. Apparatus according to claim 1, wherein each source of irradiation comprises a source of light for producing light to irradiate said fluid passageway.

3. Apparatus according to claim 2, wherein each source of light comprises at a source of ultraviolet light.

4. Apparatus according to claim 3, wherein each source of ultraviolet light comprises a microwave electrodeless discharge bulb.

5. Apparatus according to claim 4, wherein said fluid passageway has a central axis, and each bulb is a tubular bulb having a longitudinal axis substantially parallel to the central axis of said fluid passageway.

6. Apparatus according to claim 3, wherein each source of ultraviolet light comprises an arc discharge bulb.

7. Apparatus according to claim 3, wherein each source of ultraviolet light comprises a fluorescent discharge bulb.

8. Apparatus according to claim 2, wherein said fluid passageway has a central axis, and each source of light comprises a tubular bulb having a longitudinal axis substantially parallel to the central axis of said fluid passageway.

9. Apparatus according to claim 1, wherein said fluid passageway has a central axis, and each source of irradiation has a tubular shape with a longitudinal axis substantially parallel to the central axis of said fluid passageway.

10. Apparatus according to claim 1, wherein both said at least one source of irradiation and said fluid passageway are spaced from the focal axes.

11. Apparatus according to claim 10, wherein said fluid passageway is on one of the major axes.

12. Apparatus according to claim 1, wherein said fluid passageway is spaced from the major axes.

13. Apparatus according to claim 1, wherein said fluid passageway and said at least one source of irradiation are positioned so as to provide a substantially two-dimensionally uniform irradiation distribution across a cross-sectional plane of the fluid flowing in said fluid passageway.

14. Apparatus according to claim 1, wherein said fluid passageway and said at least one source of irradiation are positioned so as to provide a substantially three-dimensionally uniform irradiation distribution within a volume of fluid flowing in said fluid passageway.

15. Apparatus according to claim 1, wherein each source of irradiation is positioned between the first focal axis and the elliptical end of the respective one of said troughs.

16. Apparatus according to claim 1, wherein the second focal axes of all of said troughs are substantially coincident.

17. Apparatus according to claim 1, wherein the second focal axes of said troughs define a figure having a center of symmetry.

18. Apparatus as claimed in claim 17, wherein said source of irradiation has a longitudinal axis, and said fluid passageway has a central axis extending substantially through the center of symmetry of the figure and substantially parallel to the longitudinal axis of said source of irradiation.

19. Apparatus as claimed in claim 1, having a single source of irradiation and two troughs.

20. Apparatus as claimed in claim 19, wherein said fluid passageway is on the first focal axis of one of said elliptical troughs, and said source of irradiation is spaced from the focal axes and is adjacent the first focal axis of the other said troughs.

21. Apparatus as claimed in claim 19, wherein said source of irradiation is on the first focal axis of one of said troughs, and said fluid passageway is spaced from the focal axis and is adjacent the first focal axis of the other of said troughs.

22. Apparatus according to claim 19, wherein the major axes of said troughs coincide.

23. Apparatus as claimed in claim 19, wherein said two troughs have non-coinciding major axes.

24. Apparatus as claimed in claim 23, wherein said two troughs have parallel major axes.

25. Apparatus as claimed in claim 24, wherein said source of irradiation has a longitudinal axis, and said fluid passageway has a central axis extending between the major axes of said troughs and substantially parallel to the longitudinal axis of said source of irradiation.

26. Apparatus according to claim 23, wherein said source of irradiation is on the major axis of one of said troughs and said fluid passageway is on the major axis of the other of said troughs.

27. Apparatus as claimed in claim 1, having two sources of irradiation and two troughs.

28. Apparatus as claimed in claim 27, wherein the second focal axes of said troughs coincide, said fluid passageway is on the second focal axes, and each of said sources of irradiation is spaced from a respective one of the first focal axes.

29. Apparatus as claimed in claim 27, wherein each of said two sources of irradiation is on the first focal axis of a respective one of said troughs, and said fluid passageway is spaced from the second focal axes.

30. Apparatus according to claim 27, wherein the major axes of said troughs coincide.

31. Apparatus as claimed in claim 27, wherein said two troughs have non-coinciding major axes.

32. Apparatus as claimed in claim 31, wherein said two troughs have parallel major axes.

33. Apparatus as claimed in claim 32, wherein said sources of irradiation have parallel longitudinal axes, and said fluid passageway has a central axis extending between the major axes of said troughs and substantially parallel to the longitudinal axes of said sources of irradiation.

34. Apparatus according to claim 31, wherein said source of irradiation is on the major axis of one of said troughs and said fluid passageway is on the major axis of the other of said troughs.

35. Apparatus according to claim 1, wherein the major axis of each trough intersects the major axis of each angularly adjacent elliptical trough at an angle equal to $2\pi/N$, where N is the number of troughs.

36. Apparatus according to claim 35, wherein the major axes of the troughs intersect at a single intersection.

37. Apparatus according to claim 36, wherein said fluid passageway has a central axis passing through the intersection of the major axes.

38. Apparatus according to claim 35, wherein said fluid passageway has a central axis passing through the center of symmetry of a figure defined by the points of intersection of the major axes of said troughs.

39. Apparatus according to claim 35, having three sources of irradiation, and wherein N=3.

40. Apparatus according to claim 39, wherein the major axes of said troughs intersect at a single intersection.

41. Apparatus according to claim 40, wherein said fluid passageway has a central axis passing through the intersection of the major axes.

42. Apparatus according to claim 39, wherein said fluid passageway has a central axis passing through a figure defined by the points of intersection of the major axes of said troughs.

43. Apparatus according to claim 35, having four sources of irradiation, and wherein N=4.

44. Apparatus as claimed in claim 43, wherein the major axes of said troughs intersect at a single intersection.

45. Apparatus according to claim 44, wherein said fluid passageway has a central axis passing through the intersection of the major axes.

46. Apparatus according to claim 43, wherein said fluid passageway has a central axis passing through the center of symmetry of a figure defined by the points of intersection of the major axes of said troughs.

47. Apparatus according to claim 1, further comprising a mount for each source of irradiation, making the position of each source of irradiation adjustable so as to provide a substantially two-dimensionally uniform irradiation distribution within fluid flowing in said fluid passageway.

48. Apparatus as claimed in claim 47, wherein each mount is adapted to be adjustably positioned on a mounting surface.

49. Apparatus as claimed in claim 47, wherein each source of irradiation is adjustably mounted to said mount.

50. Apparatus according to claim 1, further comprising a mount for each source of irradiation, making the position of each source of irradiation adjustable so as to provide a substantially three-dimensionally uniform irradiation distribution within fluid flowing in said fluid passageway.

51. Apparatus as claimed in claim 50, wherein each mount is adapted to be adjustably positioned on a mounting surface.

52. Apparatus as claimed in claim 50, wherein each source of irradiation is adjustably mounted to said mount.

53. Apparatus according to claim 1, further comprising a mount for each trough, making the position of each trough adjustable so as to provide a substantially two-dimensionally uniform irradiation distribution within fluid flowing in said fluid passageway.

54. Apparatus as claimed in claim 53, wherein each mount is adapted to be adjustably positioned on a mounting surface.

55. Apparatus as claimed in claim 53, wherein each trough is adjustably mounted to one of said mounts.

56. Apparatus according to claim 1, further comprising a mount for each trough, making the position of each trough adjustable so as to provide a substantially three-dimensionally uniform irradiation distribution within fluid flowing in said fluid passageway.

57. Apparatus as claimed in claim 56, wherein each mount is adapted to be adjustably positioned on a mounting surface.

58. Apparatus as claimed in claim 56, wherein each trough is adjustably mounted to one of said mounts.

59. Apparatus according to claim 1, further comprising an adjustable mount for said fluid passageway, making the position of said fluid passageway adjustable so as to provide a substantially two-dimensionally uniform irradiation distribution within fluid flowing in said fluid passageway.

60. Apparatus as claimed in claim 59, wherein said mount is adapted to be adjustably positioned on a mounting surface.

61. Apparatus as claimed in claim 59, wherein said fluid passageway is adjustably mounted to said mount.

62. Apparatus according to claim 1, further comprising an adjustable mount for said fluid passageway, making the position of said fluid passageway adjustable so as to provide a substantially three-dimensionally uniform irradiation distribution within fluid flowing in said fluid passageway.

63. Apparatus as claimed in claim 62, wherein said mount is adapted to be adjustably positioned on a mounting surface.

64. Apparatus as claimed in claim 62, wherein said fluid passageway is adjustably mounted to said mount.

65. A method of providing a substantially two-dimensionally uniform irradiation distribution across a cross-sectional plane of a fluid flowing in a fluid passageway, said method comprising:

providing the apparatus according to claim 1;

positioning at least one of (a) said fluid passageway and (b) said at least one source of irradiation such that defocused irradiation from said at least one source of irradiation irradiates the fluid in said fluid passageway with a substantially two-dimensionally uniform irradiation distribution; and activating said at least one source of irradiation.

66. A method of providing a substantially three-dimensionally uniform irradiation distribution within a volume of a fluid flowing in a fluid passageway, said method comprising:

providing the apparatus according to claim 1;

positioning at least one of (a) said fluid passageway and (b) said at least one source of irradiation such that defocused irradiation from said at least one source of irradiation irradiates the fluid in said fluid passageway with a substantially three-dimensionally uniform irradiation distribution; and activating said at least one source of irradiation.

67. A method of providing a substantially two-dimensionally uniform irradiation distribution across a cross-sectional plane of a fluid flowing in a fluid passageway, said method comprising:

providing the apparatus according to claim 1;

shifting at least one troughs such that defocused irradiation from said at least one source of irradiation irradiates the fluid in said fluid passageway with a substantially two-dimensionally uniform irradiation distribution; and activating said at least one source of irradiation.

68. A method as claimed in claim 67, wherein said at least one trough is shifted in a direction parallel to the minor axis of such trough.

69. A method of providing a substantially uniform three-dimensional irradiation distribution within a volume of fluid flowing in a fluid passageway, said method comprising:

providing the apparatus according to claim 1;

shifting at least one trough such that defocused irradiation from said at least one source of irradiation irradiates the fluid in said fluid passageway with a substantially three-dimensionally uniform irradiation distribution; and activating said at least one source of irradiation.

70. A method as claimed in claim 69, wherein said at least one trough is shifted in a direction parallel to the minor axis of such trough.

71. A method of treating a fluid flowing in a fluid passageway, comprising:

providing the apparatus according to claim 1;

passing a fluid through said fluid passageway;

irradiating the fluid in said fluid passageway with irradiation produced by said at least one source of irradiation; and activating said at least one source of irradiation.

72. A method according to claim 71, wherein irradiating the fluid comprises irradiating the fluid with ultraviolet light.

73. A method according to claim 72, wherein said fluid includes a material to be disinfected, and wherein irradiating the fluid disinfects the material flowing in said fluid passageway.

74. A method according to claim 72, wherein the fluid includes a material to be purified, and wherein irradiating the fluid purifies the material flowing in said fluid passageway.

75. A method according to claim 72, wherein the fluid includes a material to be oxidized, and wherein irradiating the fluid causes oxidation of the material flowing in said fluid passageway.

\* \* \* \* \*